(12) United States Patent
Zhao et al.

(10) Patent No.: US 9,125,615 B2
(45) Date of Patent: Sep. 8, 2015

(54) SYSTEM AND METHOD FOR NON-INVASIVE MEASUREMENT OF CARPAL TUNNEL PRESSURE

(71) Applicant: Mayo Foundation for Medical Education and Research, Rochester, MN (US)

(72) Inventors: Chunfeng Zhao, Rochester, MN (US); Yuexiang Wang, Rochester, MN (US); Kai-Nan An, Rochester, MN (US); Peter C. Amadio, Rochester, MN (US); Xiaoming Zhang, Rochester, MN (US); James F. Greenleaf, Rochester, MN (US); Bo Qiang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/021,141

(22) Filed: Sep. 9, 2013

(65) Prior Publication Data
US 2014/0081136 A1 Mar. 20, 2014

Related U.S. Application Data

(60) Provisional application No. 61/700,945, filed on Sep. 14, 2012.

(51) Int. Cl.
*A61B 8/00* (2006.01)
*A61B 8/08* (2006.01)
*A61B 5/00* (2006.01)

(52) U.S. Cl.
CPC ............... *A61B 8/48* (2013.01); *A61B 5/0093* (2013.01); *A61B 5/4523* (2013.01); *A61B 8/485* (2013.01); *A61B 8/5223* (2013.01); *A61B 8/08* (2013.01)

(58) Field of Classification Search
CPC ........ A61B 8/00; A61B 8/52; G01N 29/0672; G01N 29/07
See application file for complete search history.

(56) References Cited

U.S. PATENT DOCUMENTS

| | | | |
|---|---|---|---|
| 5,810,731 A * | 9/1998 | Sarvazyan et al. | 600/438 |
| 7,753,847 B2 | 7/2010 | Greenleaf et al. | |
| 7,785,259 B2 | 8/2010 | Zheng et al. | |
| 8,216,148 B2 * | 7/2012 | Amadio et al. | 600/453 |
| 8,469,891 B2 * | 6/2013 | Maleke et al. | 600/438 |

OTHER PUBLICATIONS

Wang, et al., "A Non-Invasive Technique for Estimating Carpal Tunnel Pressure by Measuring Shear Wave Speed in Tendon: A Feasibility Study", Journal of Biometrics, Sep. 7, 2012, pp. 2927-2930.

* cited by examiner

*Primary Examiner* — Unsu Jung
*Assistant Examiner* — Joel Lamprecht
(74) *Attorney, Agent, or Firm* — Yakov Sidorin; Quarles & Brady LLP

(57) ABSTRACT

Method and system for non-invasive determination of a pressure characteristic associated with carpal tunnel (CT) region of a subject. Speed of a shear wave induced in the tissue of the subject and propagating through the CT region is measured at least once. The pressure characteristic is substantially proportional to determined speed.

16 Claims, 10 Drawing Sheets

SYSTEM AND METHOD FOR NON-INVASIVE MEASUREMENT OF CARPAL TUNNEL PRESSURE

CROSS-REFERENCE TO RELATED APPLICATIONS

The present application claims priority from and benefit of the U.S. Provisional Patent Application No. 61/700,945 filed on Sep. 14, 2012 and titled "System and Method for Non-Invasive Measurement of Carpal Tunnel Pressure", the disclosure of which is incorporated herein by reference.

TECHNICAL FIELD

This invention relates to characterization of carpal tunnel syndrome and, more particularly, to a non-invasive measurement of pressure in carpal tunnel with the use of shear waves acoustically generated in biological tissue.

BACKGROUND OF THE INVENTION

In the human body, the carpal tunnel or carpal canal is the passageway on the anterior side of the wrist that connects the forearm to the middle compartment of the deep plane of the palm. The tunnel includes bones and connective tissue. Several tendons and a median nerve pass through it. The carpal tunnel is narrow, and when, for various reasons, the space within the tunnel is reduced or the volume of contents of the tunnel is increased, the effective narrowing of the carpal tunnel with respect to its contents often results in the elevated carpal tunnel pressure, which leads to the median nerve becoming entrapped or compressed—a medical condition known as carpal tunnel syndrome (CTS). This compression causes paresthesia, pain, numbness of the thumb, index, long, and radial half of the ring finger and other symptoms in the distribution of the median nerve. The scientifically established treatment of the carpal tunnel syndrome includes surgery to cut the transverse carpal ligament to release the carpal tunnel pressure.

Although the close relationship of carpal tunnel pressure with median nerve dysfunction has been reported, the current methods for measuring the tunnel pressure are invasive, such as, for example, the use of a catheter inserted into the carpal canal to monitor the pressure. A noninvasive method for quantifying the carpal tunnel pressure and, in general, the pressure of any closed bodily compartment that has a tendon remains desirable.

SUMMARY OF THE INVENTION

Embodiments of the invention provide a method for determining a material characteristic of a carpal tunnel of a subject with an ultrasound system. The method includes determining a first value corresponding to a speed of propagation of a shear wave that is induced with an external input applied to a tissue of the subject in proximity to the first region that is associated with the carpal tunnel and determining a second value corresponding to a speed of propagation of such shear wave in this first region. The method further includes calculating a parameter representing pressure in the carpal tunnel region based on the first and second values. The external input may be applied to the subject at a second region outside of the carpal tunnel. In one embodiment, at least one of determining a first value and determining a second value is effectuated with the use of an ultrasound system by, for example, collecting echo data representing the shear wave. In a specific embodiment, at least one of determining a first value and determining a second value includes detecting ultrasound energy reflected from at least two detection points of the subject by insonating these at least two detection points with an amplitude-modulated ultrasound detection beam emitted by said ultrasound system.

Embodiments of the invention further provide for a method for determining a material characteristic of a carpal tunnel region of a subject with an ultrasound system that includes (i) receiving, with an ultrasound transducer, ultrasound energy reflected from one or more detection points associated with the carpal tunnel region by insonating such points with ultrasound detection pulses; (ii) determining, from so detected ultrasound energy, echo data indicative of a shear wave that is produced by applying a temporally-varying force to a vibration origin region of the subject and that propagates through the carpal tunnel region; (iii) calculating, from the determined echo data, a first set of values including (N) values representing a physical parameter of the shear wave in the carpal tunnel region, wherein (N) is greater than or equal to 1; and (iv) determining, for each of (N) values, a corresponding value of pressure of the carpal tunnel region. The method may further include (v) receiving, with an ultrasound transducer, ultrasound energy reflected from one or more detection points outside of the carpal tunnel region by insonating these detection points with ultrasound detection pulses; (vi) determining, from the detected ultrasound energy, echo data indicative of the shear wave at these detection points outside of the carpal tunnel region; (vii) calculating, from the determined echo data, a second set of values including (N) values representing a physical parameter of the shear wave at these one or more detection points outside the carpal tunnel region, wherein (N) is greater than or equal to 1; and (viii) determining a parameter representing a pressure in the carpal tunnel by comparing a difference between ($i^{th}$) values of the first and second sets of values with a difference between ($j^{th}$) values of the first and second set of values, wherein both (i) and (j) are greater than or equal to 1 and less than or equal to (N). In one embodiment, the physical parameter represented by the values from the first and second sets of values includes at least one of speed, phase, and amplitude. In a specific embodiment, determination of echo data includes determination of echo data that is indicative of a shear wave produced by insonating the vibration origin region with ultrasound detection pulses emitted by the ultrasound transducer.

DETAILED DESCRIPTION

Figure 1:
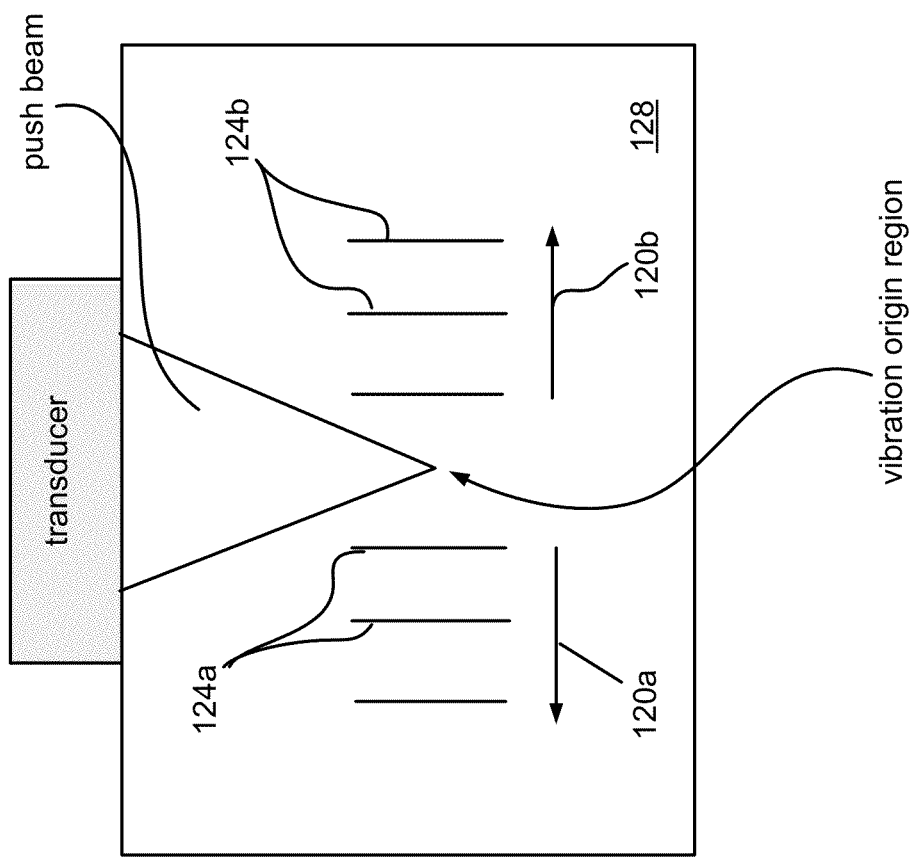
FIG. 1 is a schematic diagram illustrating the application of ultrasound pulses to the tissue to ignite vibrational motion in the tissue.

Carpal tunnel syndrome (or CTS) is a common clinical problem. Although the etiology of CTS is still unknown in most cases, it has been commonly recognized that carpal tunnel pressure is elevated in CTS patients and typically exceeds a threshold of about 30 mmHg. The pressure significantly increases during pinch and grip activities and was reported to reach as much as 1151 mmHg with maximum grip. The median nerve dysfunction correlates with these elevated pressures. Although the close relationship of carpal tunnel pressure with median nerve dysfunction has been reported, the current methods for measuring the carpal tunnel pressure (CTP) are invasive: for example, a catheter inserted into the carpal canal is used to monitor the pressure.

Changes in acoustic properties of a material caused by elastic deformation can be measured as a change in wave propagation speed or reflected wave amplitude. This is based on the principle that the acoustic properties of a material are altered as the material is deformed and loaded with pressure.

In patients with CTS, apart from the impaired median nerve function, the flexor tendons in the carpal tunnel are under the compressive load due to the increased pressure in the carpal tunnel. Existing measurements of CTP are invasive and not reliable due to technical difficulties. Although the CTP is a sensitive indicator for assessing the stage or severity of the CTS, it is not considered to be a clinical diagnostic measure. The idea of the present invention (i.e., non-invasive characterization of the pressure in carpal tunnel based on characterization of mechanical properties of the tissue associated with carpal tunnel) stems from the realization that that the acoustic properties of the flexor tendon (or other tissues such as median nerve) are different between the portion of the tendon that is outside the carpal tunnel and another portion of the tendon that is subjected to the pressure inside the tunnel. According to the idea of the present invention, a measurement of stiffness of the target tissue (including at least one of tendon, nerve, and ligament) associated with carpal tunnel is based on a change of pressure in the tunnel as compared with that outside the tunnel. Therefore, the problem of determination of the carpal tunnel pressure is solved by deriving a parameter representative of the carpal tunnel pressure from an empirically measured parameter associated with the speed of a shear wave propagating through the tissue outside the tunnel.

Measurements of mechanical properties of tissues (such as, for example, stiffness and viscosity) are often conducted with the use of ultrasound-caused shear waves, magnetic resonance elastography, microphony or other modalities. As a non-limiting example of an applicable ultrasound modality, a shear wave dispersion ultrasound vibrometry ("SDUV") can be used for such measurements. This SDUV technique is described, for example, in U.S. Pat. Nos. 7,785,259, and 7,753,847, the disclosure of each of which is incorporated by reference herein. A focused ultrasound beam, operating within FDA safety limits, is applied to a subject to generate harmonic shear waves in a tissue of interest. The propagation speed of the induced shear wave is frequency dependent, or "dispersive," and relates to the mechanical properties of the tissue of interest. Shear wave speeds at a number of frequencies are measured by pulse echo ultrasound and subsequently fit with a theoretical dispersion model to inversely solve for tissue elasticity and viscosity. These shear wave speeds are estimated from the phase of tissue vibration that is detected between two or more points with known distance along the shear wave propagation path.

One feature of the SDUV method and system is the use of a so-called "binary pushing pulse" that allows the use of a single array ultrasound transducer for both motion excitation and the echo signal detection. For example, the transducer focuses ultrasound at one location, the "vibration origin," to vibrate the tissue of interest and then electronically steers its focus to another location, a "motion detection point," for echo signal vibration detection. Instead of continuously vibrating the tissue of interest, the "pushing" ultrasound is turned on during a vibration time period to vibrate the tissue and turned off to provide a time window for the pulse echo motion detection. When the pushing pulse is off, a series of short ultrasound pulses is transmitted to the motion detection locations and a corresponding series of echo signals is received and processed to determine the tissue vibration. This intermittent pulse sequencing strategy allows both the production of a shear wave and the monitoring of its propagation at the same time with a single array transducer.

Continuing with the description of an example of an ultrasound modality applicable to measurement of mechanical properties of a biological tissue, the SDUV techniques typically use a long duration (hundreds of microseconds) pulse of a typically focused ultrasound beam to generate vibration within a subject or tissue of interest. This ultrasound, or "push," ultrasound pulse is repeatably delivered to the same (push) location within the subject, referred to herein as a vibration origin, at a chosen pulse repetition frequency ("PRF"), denoted $PRF_P$, which is typically on the order of a few kHz.

The applied push-pulse generates tissue vibration at the vibration origin, which propagates in the tissue in a form of a shear wave outwardly from the vibration origin. A shear wave can be detected at several positions, or motion-detection points, along the propagation path of the wave. As is schematically shown in FIG. 1 with arrows 120a, 120b, as the shear wave 124a, 124b propagates through the tissue 128, tissue particles are displaced away from their respective equilibrium positions. The motion of the particles (characterized by displacement, velocity, and acceleration, for example) occurs in a plane 130 that is substantially perpendicular to the direction of propagation 120a, 120b of the shear wave.

Figure 2A:
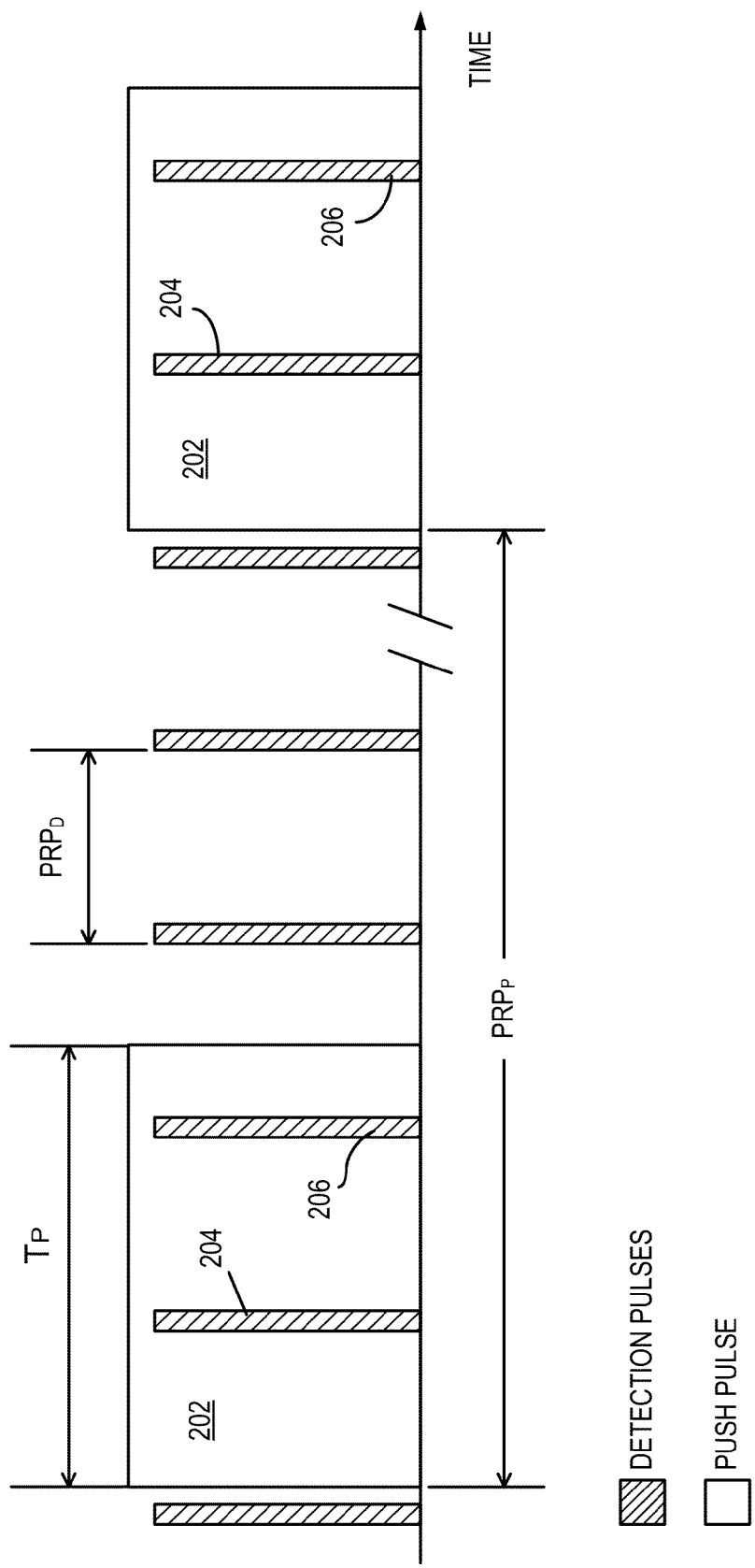
FIG. 2A is a pulse timing diagram indicating the application of ultrasonic vibration and detection pulses, in which a train of detection pulses and an ultrasonic vibration pulse having a significantly long duration overlap.
Figure 2B:
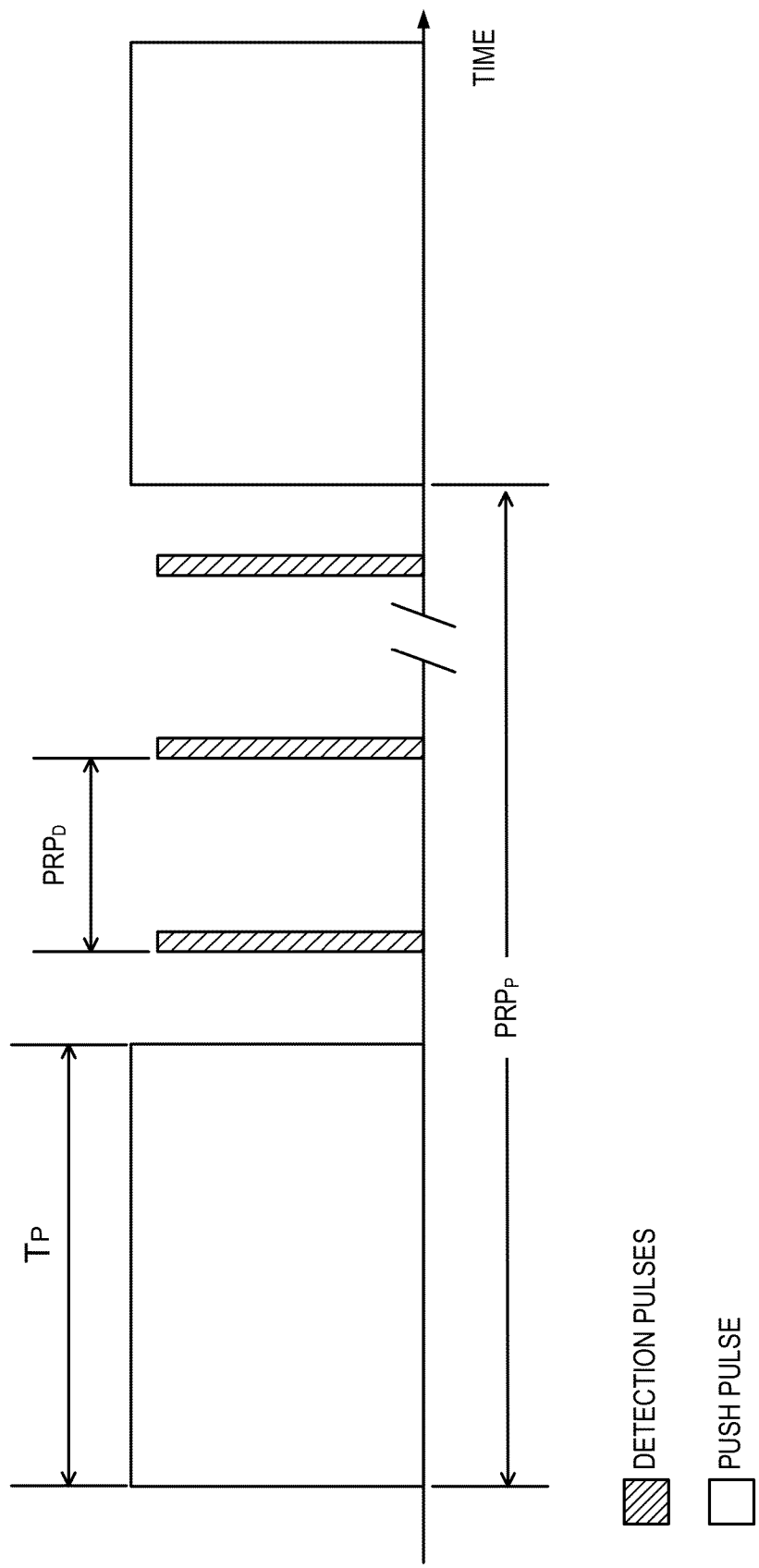
FIG. 2B is a pulse timing diagram indicating the application of ultrasonic vibration and detection pulses, in which a train of detection pulses and an ultrasonic vibration pulse having a significantly long duration alternate.

The detection of the shear wave is enabled by insonating the tissue at a chosen motion-detection point with a second, detection ultrasound beam in a pulse-echo ultrasound mode. The detection ultrasound beam is either focused or unfocused with respect to the motion-detection point of interest. The propagation speed $c_s$ of the shear wave can be calculated from the phase of the shear wave as detected at two or more motion-detection points. While FIG. 1 illustrates the generation of the shear wave with a transducer shown to be in contact with the tissue, it is understood that generally such contact is not required. Non-limiting examples of time-diagram showing the push-pulse and push-echo detection pulses is shown in FIGS. 2A and 2B. The pulse timing diagram of FIG. 2A illustrates a scheme in which a train of detection pulses (formed with a repetition period $PRP_D$) overlaps in time with long push pulses 202 (having duration $T_D$ and formed with a repetition period $PRP_D$). The pulse timing diagram of FIG. 2B illustrates a scheme in which a train of detection pulses and long duration push pulses 202 (having durations $T_D$)

alternate. It is appreciated that the above description of the SDUV was provided only as an example, and other methods of excitation and detection of shear waves in the tissue can be utilized.

Shear waves ultrasonically generated within the tissue are advantageous for the purposes of measurements in that such waves are non-invasive, do not provide any ionizing radiation, and posses propagation characteristics that are independent from both the excitation and the detection of these waves. According to an embodiment of the invention, the ultrasonically-generated shear waves in carpal tunnel are used to quantitatively evaluate the carpal tunnel pressure. The demonstrated results prove that both the speed of the shear wave and the difference in speeds associated with the wave inside and outside the carpal tunnel increase linearly with pressure in the tunnel. Accordingly, speed of shear waves measured, for example, in tendon can be used as an indicator of CTP.

Figure 3A:
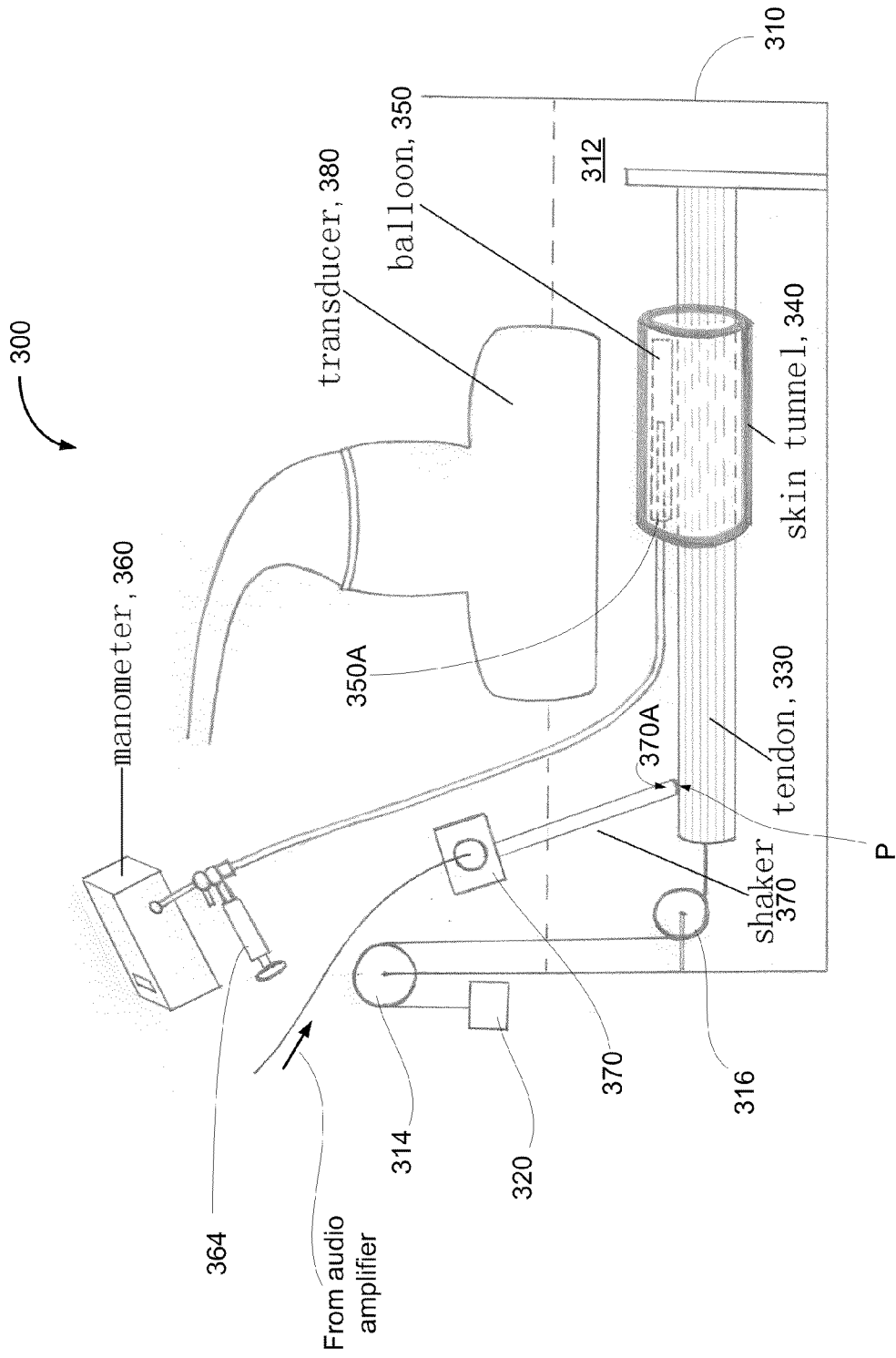
FIGS. 3A and 3B are diagrams illustrating embodiments of the measurement system of the invention.
Figure 3B:
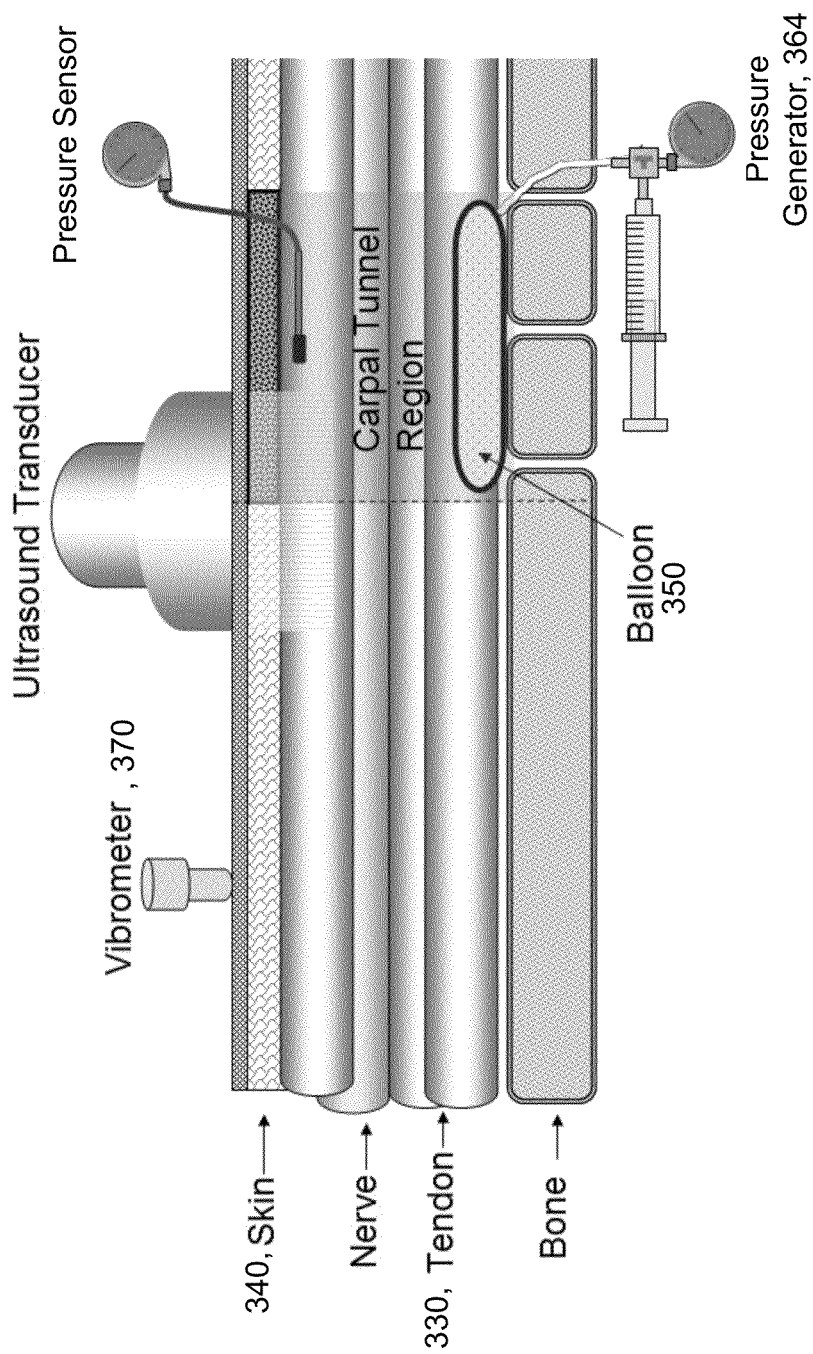

To illustrate the operability of an embodiment of the invention, a simplified experimental model was constructed to measure the shear wave speed in an Achilles tendon under different tunnel pressures. As shown in FIG. 3A, the testing device 300 included a container 310 filled with degassed saline solution 312, two pulleys 314, 316, a 5 Newton (5 N) metal weight 320 and an Achilles tendon 330. The Achilles tendon 330 was obtained from a canine cadaver, leaving the bone and insertion site intact at the distal end. The bony end of the tendon 330 was fixed at one side in the container 310. The other side of the tendon 330 was loaded with a 5 N weigh to maintain the tendon tension. The middle part of the tendon 330 was wrapped by a tubular skin tunnel 340 made of a piece of canine skin sufficiently tough to emulate, in practice, the bone-ligament carpal tunnel and yet soft enough to facilitate transmission and detection of waves from the tendon 330. The tunnel 340 was about 25 mm in length, with a diameter of about 15 mm and a wall thickness of about 2.5 mm. There was potential space between the tendon 330 and the tunnel 340. A custom-made balloon 350 with a length substantially similar to that of the tunnel 340 and a smaller diameter (of about 1 cm) was disposed into the tunnel 340. To ensure that the balloon distension is substantially uniform along its length, the balloon was made tubular with approximately the same diameter along its length. The proximal and distal sites of the balloon 350 were fixed at the skin tunnel 341 to prevent the balloon 350 from sliding and repositioning with respect to the skin tunnel 340 during the balloon pressurization. The proximal end 350A of the balloon 350 was connected to a three-way stopcock. The other two ends of the three-way stopcock were connected to a manometer 360 (Gould 0517, Oxnard, Calif.) and a 10 ml syringe 364. Air was injected into the balloon 350 to elevate the tunnel pressure, which was monitored by the manometer 360. During the measurement, the balloon 350 was not protruding outside the tunnel 330. FIG. 3B provides an additional illustration of the principle of employed measurement.

Shear wave speed in the tendon 330 was measured under the following conditions: (1) balloon 350 pressure of about 0 mm Hg; (2) balloon 350 pressure of about 10 mm Hg; (3) balloon 350 pressure of about 20 mm Hg; (4) balloon 350 pressure of about 30 mm Hg; (5) balloon 350 pressure of about 60 mm Hg; (6) balloon 350 pressure of about 90 mm Hg; (7) balloon 350 pressure of about 20 mm Hg; and (8) balloon 350 pressure of about 150 mm Hg. The shear wave speed measurement was carried out with the use of approximately 100 Hz sinusoidal audio waves, of duration of about 100 ms, generated by a function generator (Model 33120A, Agilent, Santa Clara, Calif.) and amplified by an audio amplifier.

Figure 3C:
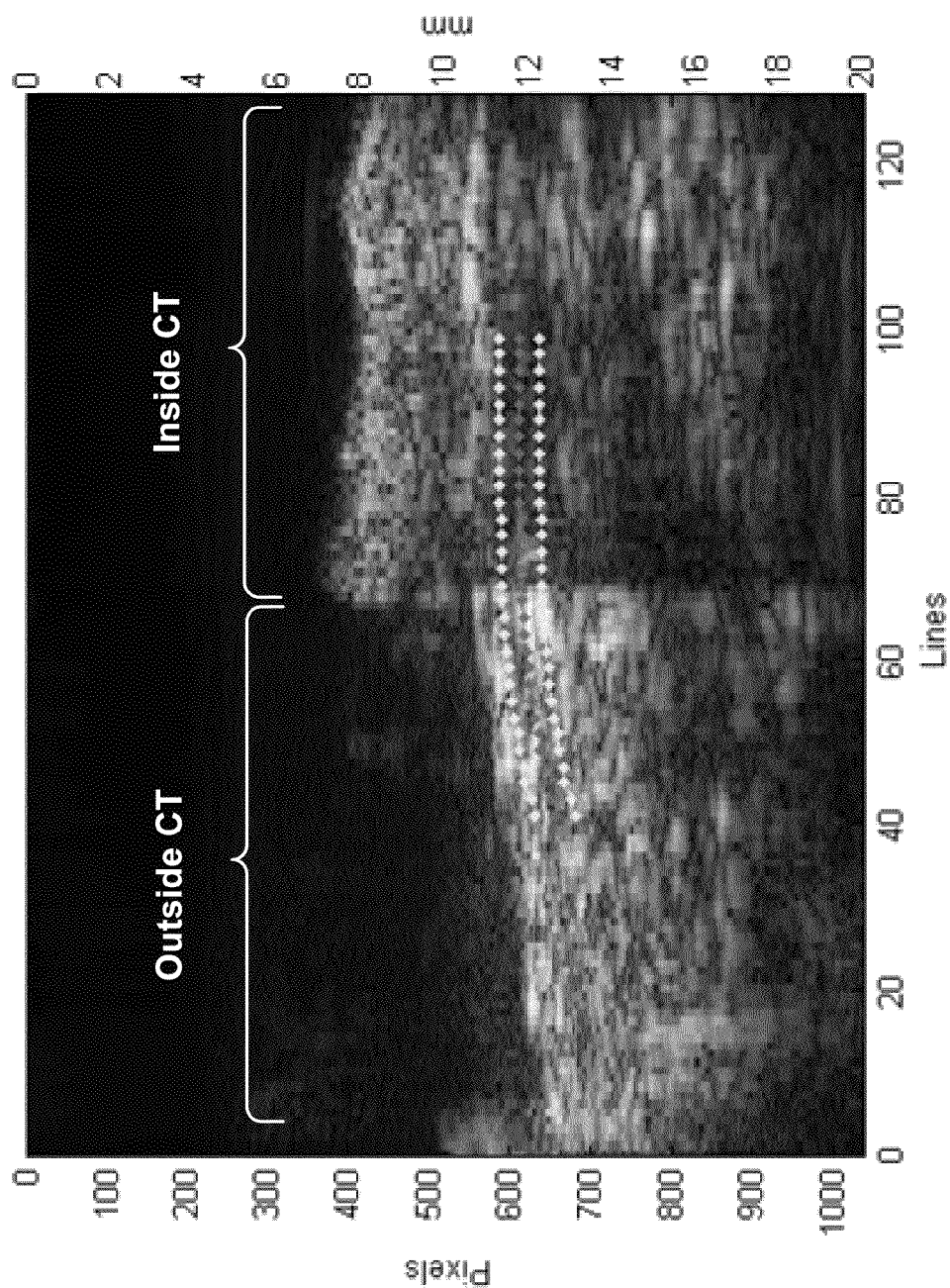
FIG. 3C is a plot illustrating data collected at a number of ultrasound lines inside the tunnel and a similar number of lines outside the tunnel 330, for each pressure level, and overlapped with an image of the carpal tunnel.

In further reference to FIGS. 3A and 3B, the amplified audio signal was used to drive an electromagnetic shaker 370, which applied a cyclical force to the tendon 330 at a vibration origin region P via a ball tip 370A (about 4 mm in diameter). The generated shear waves were detected by an ultrasound system (Model SonixRP, Ultrasonix Corporation, Calif.; not shown) with a 9.5 MHz probe 380. The transducer 380 and the tendon 330 were submerged in degassed saline solution 312 during the experiment. Data at fifteen ultrasound lines inside the tunnel 330 and fifteen lines outside the tunnel 330 were collected at each pressure level, as shown in FIG. 3C. Shear wave speed was estimated using a phase gradient method, discussed, for example in (Zhang, X., Greenleaf, J. F.; Estimation of tissue's elasticity with surface wave speed. In *Journal of the Acoustical Society of America* 122, 2522-2525; 2007 Zhang, X., Qiang, B., Greenleaf, J., Comparison of the surface wave method and the indentation method for measuring the elasticity of gelatin phantoms of different concentrations, in *Ultrasonics* 51, 157-164, 2011) and providing a linear relationship of $v=|2\pi f/\alpha|$ between the speed of the shear wave v, the excitation frequency f (in Hz), and the slope $\alpha$ of the linear regression between the phase delay and distance.

Figure 4A:
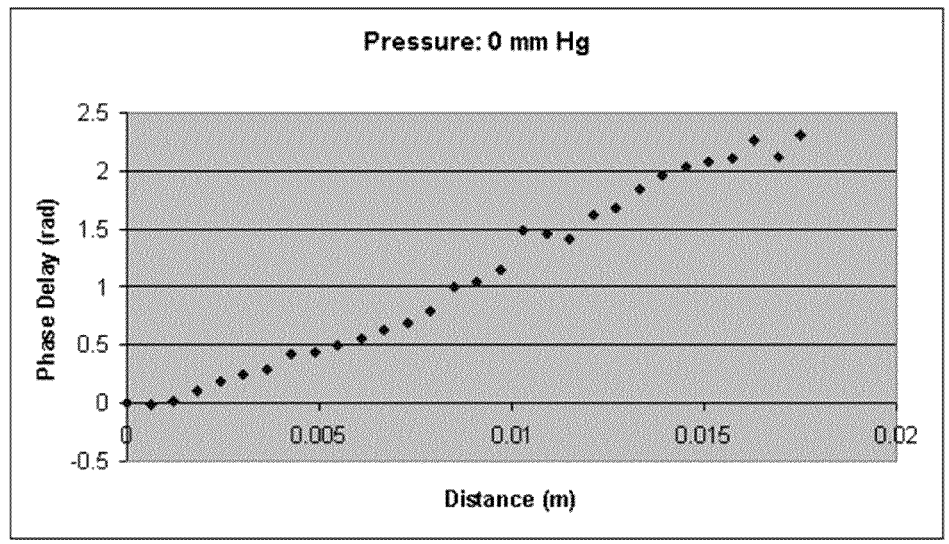
FIGS. 4A and 4B are plots showing dependencies of phase delay of a shear wave propagating through the carpal tunnel as functions of a distance from the region of origin of such wave, for different values of pressure in the carpal tunnel.
Figure 4B:
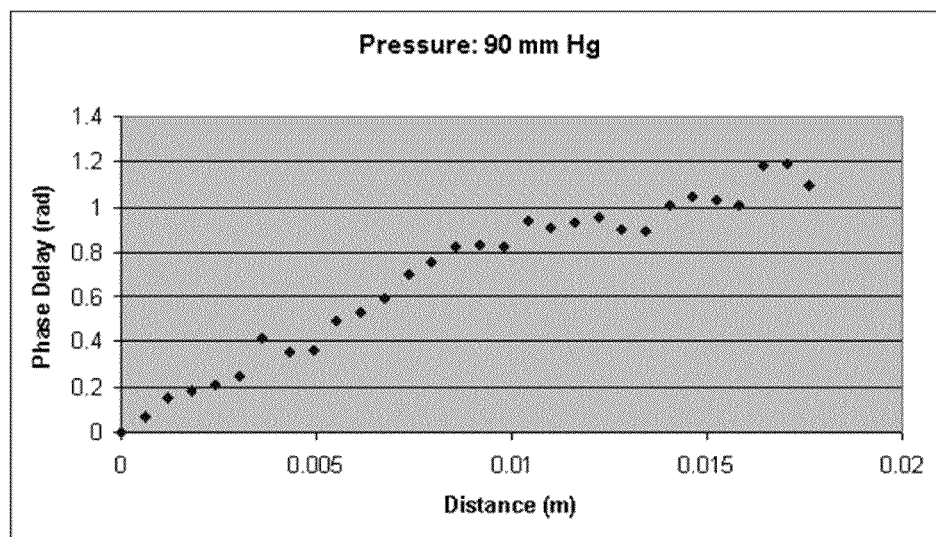

FIGS. 4A and 4B illustrate dependencies of phase delay of wave propagation as a function of distance from the vibration origin region P for pressure levels of about 0 mm Hg and 90 mm Hg.

Once the predetermined pressure level was reached, such pressure was maintained for the duration of the measurement. After each speed measurement was completed, the balloon 350 was de-pressurized down to about 0 mm Hg and allowed to rest for about 2 minutes before the balloon 350 was pressurized again for the next data collection cycle. At each pressure level, the measurement of wave propagation speed measurement was repeated twice to eliminate unwanted measurement errors.

The results from the two measurements are listed in Table 1.

TABLE 1

| | Wave Propagation Velocity (m/s) | | | | | |
|---|---|---|---|---|---|---|
| | First Measurement | | | Second Measurement | | |
| Tunnel Pressure (mm Hg) | Outside the Tunnel | Inside the Tunnel | Difference between pressure values inside and outside the tunnel | Outside the Tunnel | Inside the Tunnel | Difference between pressure values inside and outside the tunnel |
| 0 | 6.29 | 6.83 | 0.54 | 6.78 | 7.78 | 0.99 |
| 10 | 6.59 | 7.38 | 0.78 | 6.82 | 7.83 | 1.01 |
| 20 | 5.93 | 8.11 | 2.18 | 6.08 | 8.81 | 2.73 |
| 30 | 6.09 | 10.61 | 4.52 | 6.57 | 12.41 | 5.84 |
| 60 | 5.33 | 12.29 | 6.96 | 6.11 | 14.79 | 8.68 |
| 90 | 6.47 | 16.10 | 9.64 | 7.27 | 17.38 | 10.11 |
| 120 | 6.42 | 17.95 | 11.53 | 5.83 | 19.23 | 13.40 |
| 150 | 6.89 | 28.00 | 21.11 | 6.41 | 28.67 | 22.25 |

Figure 5:
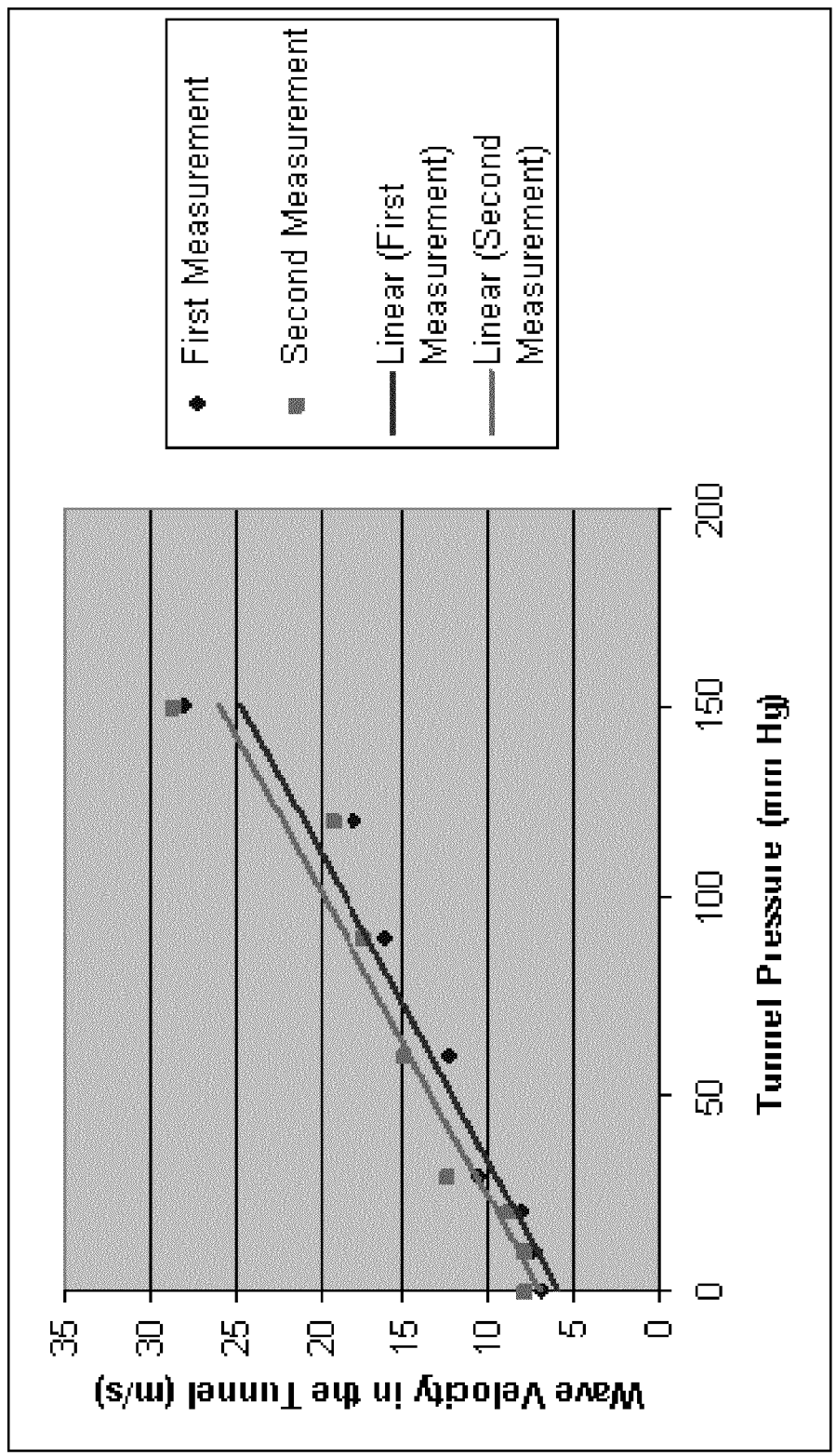
FIGS. 5 and 6 are plots showing linear dependencies of a shear wave speed on pressure in carpal tunnel determined with an embodiment of FIG. 3A.
Figure 6:
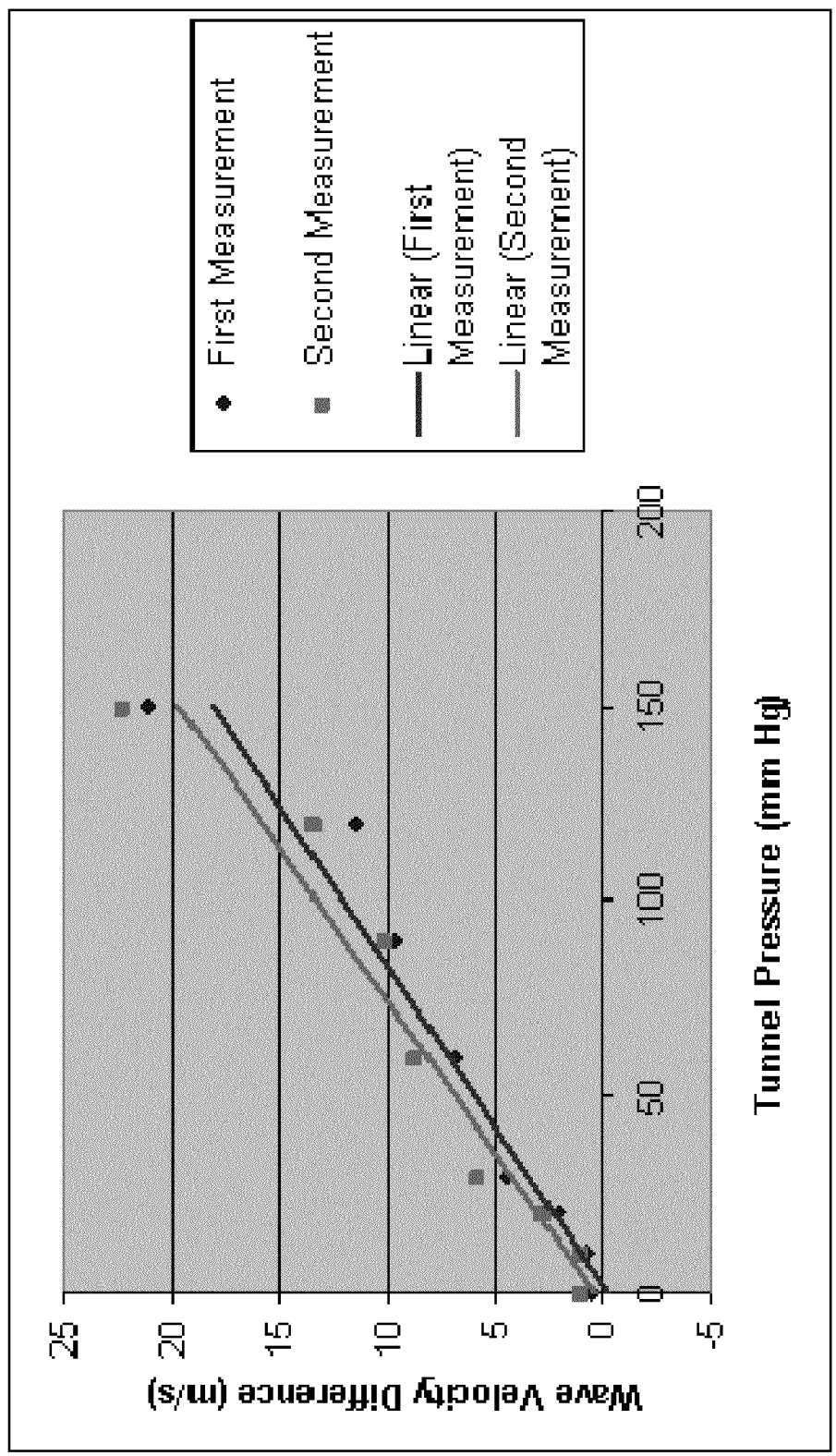

In further reference to FIG. 3, at 0 mm Hg, the average wave speed in the tendon 330 was about 7.30 m/s in the skin tunnel 340 and about 6.54 m/s outside the skin tunnel 340. In reference to FIG. 5, the wave speed in the tunnel 340 was increased from about 7.30 cm/s at 0 mm Hg to about 28.33 m/s at 150 mm Hg. The collected data supports the conclusion that the wave speed in the tunnel is in a linear relationship with the pressure in the tunnel (first measurement: $r=0.966$, $P<0.001$; second measurement: $r=0.970$, $P<0.001$) (see FIG. 5, which illustrates the absolute value of the wave speed within the CT). The speed difference between the inside-tunnel wave and outside-tunnel wave had a linear relationship with the tunnel pressure (first measurement: $r=0.969$, $P<0.001$; second measurement: $r=0.973$, $P<0.001$). FIG. 6, which illustrates the difference between wave speed values outside the CT and inside the CT).

According to an embodiment of the invention, a non-invasive measurement of the speed of propagation of a shear wave through a component of the carpal region was effectuated to measure the carpal tunnel pressure. Specifically, a tendon was used as a strain gauge to evaluate the tunnel pressure by detecting the changes of the wave propagation speed. The empirical results showed that both the absolute wave speed and the speed difference between the regions inside and outside of the carpal tunnel increase substantially linearly with the tunnel pressure, demonstrating that measurements of the shear wave speed in the tissue and, in particular, in a tissue region outside of the tunnel can be used as an indicator of carpal tunnel pressure.

Figure 7:
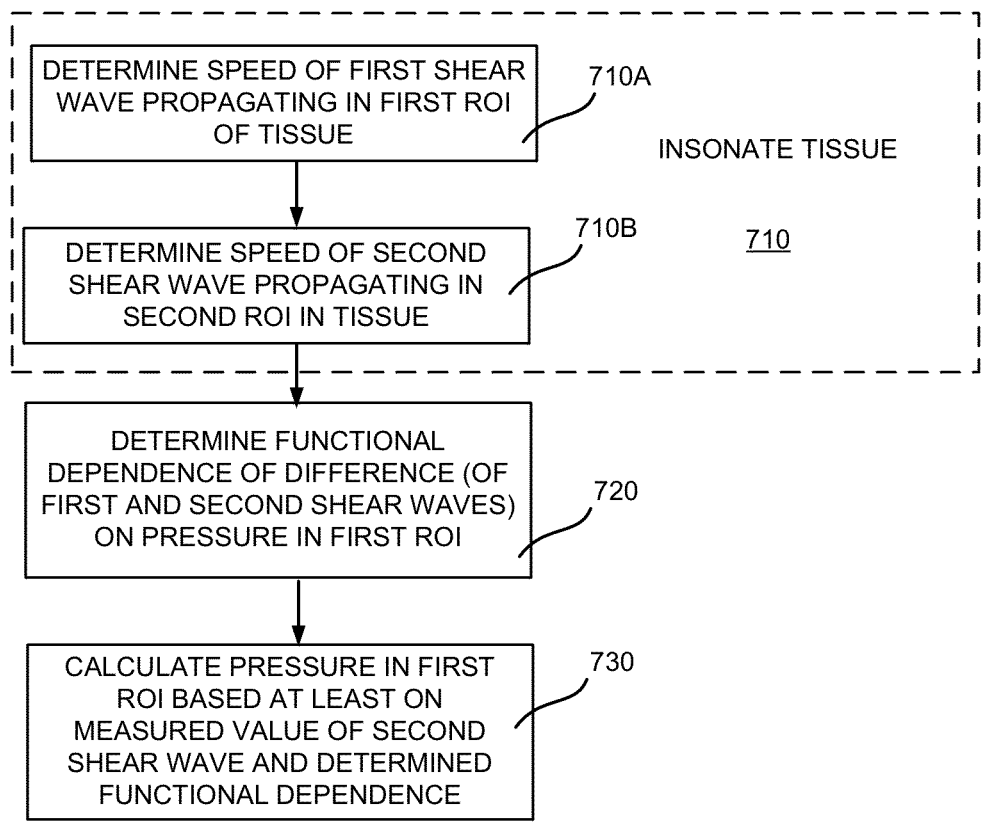
FIG. 7 is a flow chart illustrating an embodiment of the invention.

An example of the method of assessment of the carpal tunnel pressure is schematically presented in FIG. 7. Here, during the insonation, at step 710, of the tissue including the carpal tunnel, the determination is made, at step 720, about the difference between the speeds of the first shear wave (formed in the tissue as a results of the insonation and propagating through the first region of interest, ROI, including the carpal tunnel, step 710A) and a second shear wave (formed in the tissue as a result of insonation and propagating through the second ROI outside of the first ROI, step 710B) and the dependence of such difference in speeds on the internal pressure of the carpal tunnel. As a result of such determination or multiple determinations, the training data are formed based on which a further assessment of the instantaneous pressure in a carpal tunnel of a particular patient can be further made, at step 730, based on a non-invasive measurement of the speed of propagation of the shear wave specific to such patient. It is understood that the process of insonation of the tissue may include insonation of at least two detection points at the tissue with an amplitude-modulated ultrasound beam, while the process of determination of the speed of a shear wave may include receiving, with the ultrasound transducer, ultrasound energy reflected from at least one detection point. Such reflected energy, represented by the echo data acquired with the transducer, is indicative of a shear wave produced by applying a temporally-varying force to a tissue point. The insonation of at least two detection points at the tissue The following notes are in order. References made throughout this specification to "one embodiment," "an embodiment," "a related embodiment," or similar language mean that a particular feature, structure, or characteristic described in connection with the referred to "embodiment" is included in at least one embodiment of the present invention. Thus, appearances of these phrases and terms may, but do not necessarily, refer to the same implementation. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. It is understood that in the drawings, the depicted structural elements are generally not to scale, and certain components may be enlarged relative to the other components for purposes of emphasis and clarity of understanding. It is also to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, the depicted order and labeled steps of the logical flow of the described process are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method.

The invention as recited in claims appended to this disclosure is intended to be assessed in light of the disclosure as a whole, including features disclosed in prior art to which reference is made.

The present invention has been described in terms of one or more preferred embodiments, and it should be appreciated that many equivalents, alternatives, variations, and modifications, aside from those expressly stated, are possible and within the scope of the invention. For example, a gradual build-up of hydrostatic pressure in carpal tunnel the in vivo situation, taken separately or in combination with soft tissue pathological changes (such as edema, fibrosis and tissue hypertrophy, for example), may affect the coefficient of proportionality between the shear wave speed and the sought after pressure. Similarly, in a practical situation there are nine flexor tendons and the median nerve compacted in the carpal tunnel, all surrounded by subsynovial connective tissue (as compared to the simplified model used to prove the operability of an embodiment of the present invention). Furthermore, in an alternative embodiment, the wave speeds could be measured simultaneously inside the tunnel and outside the tunnel, thereby permitting valid comparison of measured values and eliminating effects from the secondary measurement factors (such as tendon tension and/or the influence of frequency of the wave source, for example). In addition, it is appreciated that the proposed methodology is generally advantageous for measurement of the pressure in any closed compartment that has a tendon or tendon equivalent inside init that could be set to vibrating. Such measurement is, therefore, within the scope of the invention. The implementation of the idea of the invention cannot be viewed as limited to the described examples of embodiments.

What is claimed is:

1. A method for determining a material characteristic of a closed compartment of a body of a subject with an ultrasound system, the closed compartment having a tendon, the method comprising:
   with a transducer of said ultrasound system, non-invasively determining a first value corresponding to a speed of propagation of a shear wave induced, with an external input applied to a tissue of the subject, in proximity to the closed compartment;
   with a transducer of said ultrasound system, non-invasively determining a second value corresponding to a speed of propagation of said shear wave in tissue in a region associated with the closed compartment;
   with a processor of said system, calculating a current value of pressure in the closed compartment by applying a functional relationship between said pressure and said speed to the first and second values, said functional relationship having been measured on a testing device that contains a model of said closed compartment; and
   outputting data representing the current value of pressure in the closed compartment.

2. A method according to claim 1, wherein said external input is applied to the tissue at a region outside of the closed compartment.

3. A method according to claim 1, wherein at least one of said determining a first value and said determining a second value is effectuated with the use of an ultrasound system, and wherein said calculating includes calculating a parameter representing instantaneous pressure in the closed compartment based on a pre-determined functional dependence of at least one of said first and second values on pressure in the closed compartment.

4. A method according to claim 1, wherein at least one of said determining a first value and said determining a second value includes detecting ultrasound energy reflected from at least two detection points of the subject by insonating said at least two detection points with an amplitude-modulated ultrasound detection beam emitted by said ultrasound system.

5. A method according to claim 1, wherein the closed compartment having a tendon includes a carpal tunnel and said pressure is carpal tunnel pressure.

6. A method according to claim 1, further comprising receiving, with an ultrasound transducer, ultrasound energy reflected from at least one detection point in a region associated with the closed compartment by insonating said at least one detection point with ultrasound detection pulses.

7. A method according to claim 6, further comprising determining, from said received ultrasound energy, echo data indicative of a shear wave that is produced by applying a temporally-varying force to a vibration origin region of the subject and that propagates through the region associated with the region associated with the closed compartment.

8. A method according to claim 7, further comprising
   calculating, from said echo data, a first set of values including (N) values representing a physical parameter of said shear wave in the region associated with the closed compartment, wherein (N) is greater than or equal to 1; and
   determining, for each of (N) values, a corresponding value of pressure of the region associated with the closed compartment.

9. A method for determining a material characteristic of a region of a closed bodily compartment of a subject with an ultrasound system, the closed bodily compartment having a tendon, the method comprising:
   receiving, with an ultrasound transducer of said ultrasound system, ultrasound energy reflected from at least one detection point associated with the region of the closed bodily compartment by insonating said at least one detection point with ultrasound detection pulses;
   determining, from said ultrasound energy, echo data indicative of a shear wave that is produced by applying a temporally-varying force to a vibration origin region of the subject and that propagates through the region of the closed bodily compartment,
   with a processor operably connected with said ultrasound transducer:
      calculating, from said echo data, a first set values including N values representing a physical parameter of said shear wave in the region of the closed bodily compartment, wherein N is greater than or equal to 1, and
      calculating a current value of pressure in the closed compartment by applying a functional relationship between said pressure and said speed to the first and second values, said functional relationship having been measured on a testing device that contains a model of said closed compartment.

10. A method according to claim 1, wherein said calculating a current value of pressure includes determining said current value of pressure in the closed compartment by determining to which reference pressure values said first and second values correspond in a look-up table, said look-up table containing data representing a linear fit to results of a reference measurement of pressure in said model of closed compartment as a function of speed of propagation of a shear wave through said model of closed compartment.

11. A method according to claim 9, wherein said calculating a current value of pressure includes determining a corresponding current value of said pressure for each of the N values.

12. A method according to claim 9, further comprising:
   receiving, with an ultrasound transducer, ultrasound energy reflected from at least one detection point outside of the region of the closed bodily compartment by insonating said at least one detection point with ultrasound detection pulses;
   determining, from said detected ultrasound energy, echo data indicative of the shear wave at said at least one detection point outside of the region of the closed bodily compartment;
   with the processor,
      calculating, from said echo data, a second set of values including N values representing a physical parameter of said shear wave at said at least one detection point outside the region of the closed bodily compartment, wherein N is greater than or equal to 1; and
      determining a parameter representing a pressure in the region of the closed bodily compartment by comparing a difference between ($i^{th}$) values of the first and second sets of values with a difference between ($j^{th}$) values of the first and second set of values, wherein both (i) and (j) are greater than or equal to 1 and less than or equal to (N) N.

13. A method according to claim 12, wherein said determining said echo data includes determining echo data indicative of a shear wave that is produced by insonating said vibration origin region with ultrasound detection pulses emitted by the ultrasound transducer.

14. A method according to claim 9, wherein the closed bodily compartment includes a carpal tunnel and said pressure is carpal tunnel pressure.

15. A method according to claim 9, wherein said physical parameter includes at least one of speed, phase, and amplitude.

16. A method according to claim 9, wherein said calculating a current value of pressure includes determining said current value of pressure in the closed compartment by determining to which reference pressure values said first and second values correspond in a look-up table, said look-up table containing data representing a linear fit to results of a reference measurement of pressure in said model of closed compartment as a function of speed of propagation of a shear wave through said model of closed compartment.

\* \* \* \* \*